(12) United States Patent
Fuchigami et al.

(10) Patent No.: US 11,328,414 B2
(45) Date of Patent: May 10, 2022

(54) PRIORITY JUDGEMENT DEVICE, METHOD, AND PROGRAM

(71) Applicant: FUJIFILM Corporation, Tokyo (JP)

(72) Inventors: Takuya Fuchigami, Tokyo (JP); Mizuki Takei, Tokyo (JP); Sadato Akahori, Tokyo (JP); Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/680,519

(22) Filed: Nov. 12, 2019

(65) Prior Publication Data

US 2020/0160516 A1 May 21, 2020

(30) Foreign Application Priority Data

Nov. 20, 2018 (JP) .............................. JP2018-217755

(51) Int. Cl.
| | | |
|---|---|---|
| *G06K 9/00* | (2022.01) | |
| *G06T 7/00* | (2017.01) | |
| *A61B 6/03* | (2006.01) | |
| *G16H 30/20* | (2018.01) | |
| *A61B 5/00* | (2006.01) | |
| *G16H 30/40* | (2018.01) | |
| *G16H 50/20* | (2018.01) | |

(52) U.S. Cl.
CPC .......... *G06T 7/0012* (2013.01); *A61B 5/0055* (2013.01); *A61B 6/032* (2013.01); *G16H 30/20* (2018.01); *G16H 30/40* (2018.01); *G16H 50/20* (2018.01); *G06T 2207/10072* (2013.01); *G06T 2207/30004* (2013.01)

(58) Field of Classification Search
None
See application file for complete search history.

(56) References Cited

U.S. PATENT DOCUMENTS

| 8,897,533 | B2 | 11/2014 | Shibata et al. | |
|---|---|---|---|---|
| 9,412,047 | B2 | 8/2016 | Matsumoto | |
| 2016/0180042 | A1* | 6/2016 | Menon | G16H 30/20 |
| | | | | 705/2 |
| 2017/0337343 | A1* | 11/2017 | Kakadiaris | G16H 50/50 |
| 2019/0228524 | A1* | 7/2019 | Chen | G16H 30/20 |
| 2020/0111558 | A1 | 4/2020 | Matsumoto et al. | |

FOREIGN PATENT DOCUMENTS

| JP | 2006325640 | 12/2006 |
|---|---|---|
| JP | 2007094513 | 4/2007 |
| JP | 2012016480 | 1/2012 |
| JP | 2012090923 | 5/2012 |
| JP | 2015102944 | 6/2015 |
| JP | 2017189237 | 10/2017 |
| JP | 2020060857 | 4/2020 |

OTHER PUBLICATIONS

"Office Action of Japan Counterpart Application" with English translation thereof, dated Dec. 14, 2021, p. 1-p. 8.

* cited by examiner

*Primary Examiner* — Wei Wen Yang
(74) *Attorney, Agent, or Firm* — JCIPRNET (57) ABSTRACT

An analysis result acquisition unit acquires an analysis result of a medical image. A medical information acquisition unit acquires medical information different from the medical image. A priority deriving unit derives a priority of the medical image based on the analysis result and the medical information.

7 Claims, 4 Drawing Sheets

PRIORITY JUDGEMENT DEVICE, METHOD, AND PROGRAM

CROSS REFERENCE TO RELATED APPLICATIONS

The present application claims priority under 35 U.S.C. § 119 to Japanese Patent Application No. 2018-217755 filed on Nov. 20, 2018. The above application is hereby expressly incorporated by reference, in its entirety, into the present application.

BACKGROUND

Technical Field

The present disclosure relates to priority judgement device, method, and program which judge a priority at the time of radiologic interpretation of a medical image and examining, diagnosing, and treating a patient by using the medical image.

Related Art

In recent years, with advances in medical devices such as a computed tomography (CT) device and a magnetic resonance imaging (MRI) device, it is possible to perform image diagnosis by using a medical image with higher quality and high resolution. In particular, in a case where the brain is used as a target part, since it is possible to specify a region in which a vascular disorder such as a cerebral infarction or cerebral hemorrhage occurs by performing image diagnosis using a CT image and an MRI image, it is possible to appropriately perform treatment based on the specified result.

A bleeding region, an infarct region, and a bleeding volume within the brain and an ischemic region in the heart are extracted by analyzing the medical image through computer-aided diagnosis (CAD) using a discriminator that learns through deep learning, and the extracted regions are acquired as these analysis results. As stated above, the analysis results generated by an analysis process are stored in association with examination information such as a patient name, a gender, an age, and a modality that acquires the medical image in a database, and the stored analysis results are used for diagnosis. In this case, a technician of a radiology department that acquires the medical image determines a radiologist corresponding to the medical image, and notifies the determined radiologist that the medical image and the analysis result are present through the CAD. The radiologist interprets the medical image while referring to the delivered medical image and analysis result, and creates a radiologic interpretation report in a radiologic interpretation terminal of the radiologist. The medical examiner treats the patient while observing the medical image and referring to the radiologic report.

A radiologic interpretation list of the medical image to be interpreted is sent to a radiologic interpretation terminal at the time of radiologic interpretation of the medical image. The aforementioned examination information is included in the radiologic interpretation list. As stated above, at the time of displaying the radiologic interpretation list on the radiologic interpretation terminal, a method of displaying the medical image desired to be interpreted on a higher layer of the radiologic interpretation list is suggested (see JP2007-094513A). In the method described in JP2007-094513A, an order of examinations to be interpreted is determined based on status information indicating a priority order of emergency, urgent, and normal radiologic interpretations.

The status information used in the method described in JP2007-094513A is included in an examination order. However, it is determined whether or not the radiologic interpretation of the acquired image is urgent based on a result of a medical examination by interview by a doctor at a stage of performing the examination order. Thus, in a case where the radiologic interpretation sees the image, there is a possibility that an event that the radiologic interpretation of the image is not so urgent is to occur. In this case, there is a possibility that the radiologic interpretation of the image that is really urgent is to be delayed. This is a problem that may occur not only in the radiologic interpretation but also at the time of determining the priority in a case where the patient is treated.

SUMMARY OF THE INVENTION

The present disclosure has been made in view of the aforementioned circumstances, and an object of the present disclosure is to appropriately judge a priority at the time of radiologic interpretation of a medical image and examining, diagnosing, and treating a patient by using the medical image.

A priority judgement device according to the present disclosure comprises an analysis result acquisition unit that acquires an analysis result for a medical image as a priority judgement target, a medical information acquisition unit that acquires medical information which is related to the medical image and is different from the medical image, and a priority deriving unit that derives a priority of the medical image based on the analysis result and the medical information.

The "medical information" includes any information related to medical use. In the present disclosure, it is assumed that the medical image is also included in one of the medical information.

In the priority judgement device according to the present disclosure, the analysis result acquisition unit may acquire the analysis result by analyzing the medical image.

The priority judgement device according to the present disclosure may further comprise a display controller that displays information regarding the medical image and information of the priority in association with each other for a plurality of the medical images on a display unit.

In the priority judgement device according to the present disclosure, the medical information may include at least one of another medical image different from the medical image, another analysis result which is an analysis result for the other medical image, or clinical information of a patient for which the medical image is acquired.

The other medical image means any image different from the medical image as the target for judging the priority. For example, the other medical image includes a medical image acquired by a modality different from the modality that acquires the medical image as the priority judgement target, medical images having different imaging dates in the same modality, and a differential image between the current medical image as the priority judgement target and the other medical image.

Any information acquired for any period, such as information of symptoms such as pain and paralysis, a location of symptom, a time elapsing after symptoms occurs, and an age of the patient, which is acquired from a medical examination by interview, diagnosis, and an ambulance crew in a case where the patient is emergency transported can be used as the clinical information of the patient.

In the priority judgement device according to the present disclosure, the medical image is a CT image, the analysis result acquisition unit acquires, as the analysis result, a first certainty factor indicating that each pixel of the CT image is infarcted, the medical information acquisition unit acquires, as the medical information, a second certainty factor indicating that each pixel of an MRI image of a patient, for which the medical image is acquired is infarcted, and the priority deriving unit derives a higher priority as the number of pixels of which a total certainty factor based on the first certainty factor and the second certainty factor is equal to or greater than a predetermined first threshold value becomes larger on the CT image.

In the priority judgement device according to the present disclosure, the medical image may be a CT image, the analysis result acquisition unit may acquire, as the analysis result, a first certainty factor indicating that each pixel of the CT image is infarcted, the medical information acquisition unit may acquire, as the medical information, part information indicating a paralyzed part of a patient for which the medical image is acquired, and the priority deriving unit may weight the first certainty factor according to the part information, and derives a higher priority as the number of pixels of which the weighted first certainty factor is equal to or greater than a predetermined second threshold value becomes larger on the CT image.

The infarction may be a hyperacute infarction. The hyperacute infarction is an infarction within 24 hours from pathogenesis.

In the priority judgement device according to the present disclosure, the medical image may be a CT image, the analysis result acquisition unit may acquire, as the analysis result, a bleeding certainty factor indicating that each pixel of the CT image is a subarachnoid hemorrhage region, the medical information acquisition unit may acquire, as the medical information, clinical information indicating whether subarachnoid hemorrhage is caused by traumatic bleeding or an aneurysm rupture for a patient for which the medical image is acquired, and the priority deriving unit may set a predetermined third threshold value to be low, in a case where the clinical information is the aneurysm rupture at the time of deriving a higher priority as the number of pixels of which the bleeding certainty factor is equal to or greater than the third threshold value becomes larger on the CT image.

A priority judgement method according to the present disclosure comprises acquiring an analysis result for a medical image as a priority judgement target, acquiring medical information which is related to the medical image and is different from the medical image, and deriving a priority of the medical image based on the analysis result and the medical information.

There is provided a program causing a computer to execute a priority judgement method according to the present disclosure.

There is provided a priority judgement device according to the present disclosure comprising a memory that stores a command to be executed by a computer, and a processor configured to execute the stored command. The process acquires an analysis result for a medical image as a priority judgement target, acquires medical information which is related to the medical image and is different from the medical image, and derives a priority of the medical image based on the analysis result and the medical information.

According to the present disclosure, it is possible to appropriately judge the priority at the time of radiologic interpretation of a medical image and examining, diagnosing, and treating a patient by using the medical image.

DETAILED DESCRIPTION

Figure 1:
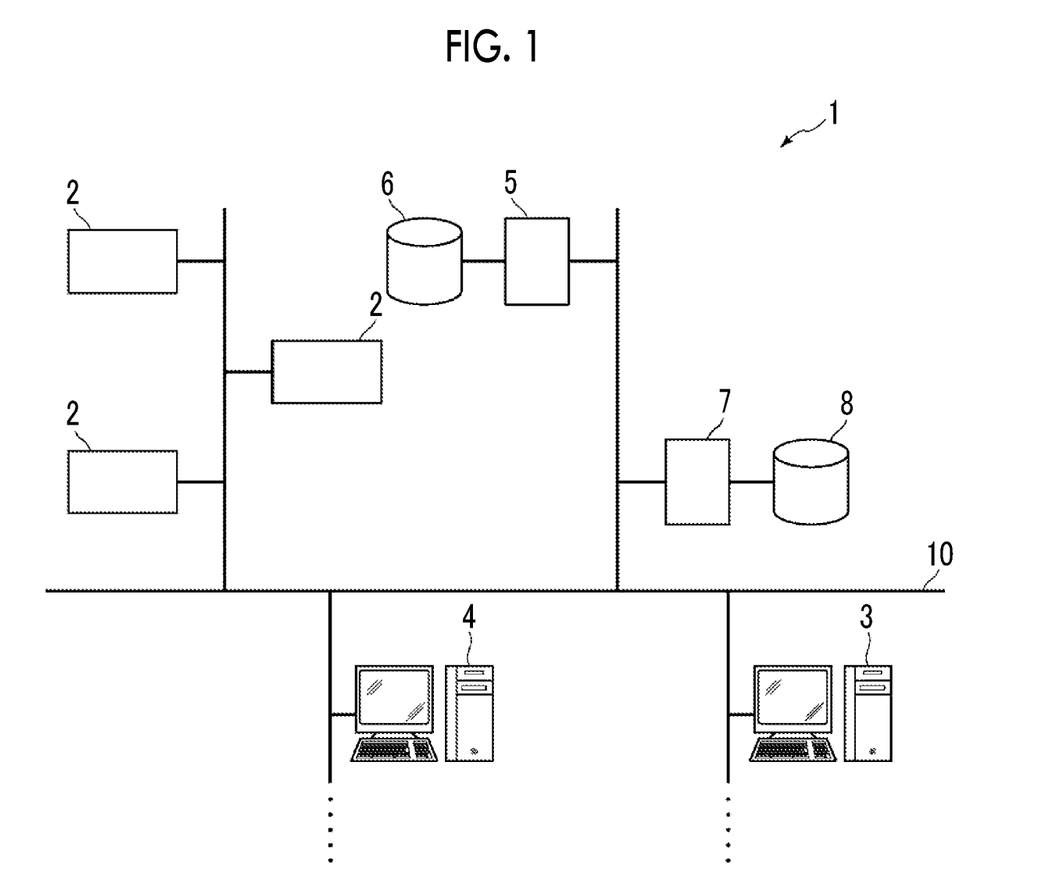
FIG. 1 is a diagram showing a schematic configuration of a medical information system to which a priority judgement device according to an embodiment of the present disclosure.

Hereinafter, an embodiment of the present disclosure will be described with reference to the drawings. FIG. 1 is a diagram showing a schematic configuration of a medical information system to which a priority judgement device according to the embodiment of the present disclosure is applied. A medical information system 1 shown in FIG. 1 is a system that performs imaging of an examination target part of a patient which is a subject, storing of a medical image obtained by imaging, radiologic interpretations and creation of a radiologic interpretation report by a radiologist, viewing of the interpretation report and detailed observation of the medical image of the radiologic interpretation target by the doctor of the hospital department as a requestor based on examination data from a doctor of a hospital department using a known ordering system.

As shown in FIG. 1, the medical information system 1 is configured such that a plurality of modalities 2, a plurality of workstations (WSs) 3 which is radiologic interpretation terminals, hospital department workstations (WSs) 4, a medical information management server 5, a medical information database 6, a radiologic interpretation report server 7, and a radiologic interpretation report database 8 are connected so as to be communicated with each other via a network 10.

Each device is a computer on which an application program for causing the computer to function as components of the medical information system 1 is installed. The application program is distributed while being recorded in a recording medium such as a digital versatile disc (DVD) or a compact disc read only memory (CD-ROM), and is installed on the computer from the recording medium. Alternatively, the application program is stored in a storage device of a server computer connected to a network or a network storage so as to be accessible from the outside, and is downloaded to and installed on the computer if necessary.

The modality 2 is a device that acquires the medical image indicating a diagnostic target part by imaging a part as the diagnostic target of the subject. Specifically, a CT device, an MRI device, a positron emission tomography (PET) device, and a computed radiography (CR) device.

The radiologic interpretation WS 3 is a computer used by the radiologist of the medical image in order to image the medical image and create the radiologic interpretation report, and includes a processing unit, a display unit such as a high-definition display, and an input unit such as a keyboard and a mouse. The radiologic interpretation WS 3 includes the priority judgement device according to the present embodiment. The priority judgement device according to the present embodiment will be described below. In the radiologic interpretation WS 3, various processes such as a viewing request for the medical image to be transmitted to the medical information management server 5, various image processing on the medical image received from the medical information management server 5, supporting for the creation of the radiologic interpretation report, a registration request and a viewing request of the radiologic interpretation report to be transmitted to the radiologic interpretation report server 7, and displaying of the radiologic interpretation report received from the radiologic interpretation report server 7 are performed by executing software programs for the various processes. Among these processes, since processes other than the processes performed by the priority judgement device according to the present embodiment are performed by the known software programs, the detailed description will be omitted.

The hospital department WS 4 is a computer used by the doctor of the hospital department in order to perform the detailed observation of the image, the viewing of the radiologic interpretation report, and the creation of an electronic medical record, and includes a processing unit, a display unit such as a high-definition display, and an input unit such as a keyboard and a mouse. In the hospital department WS 4, various processes such as a viewing request for the medical information to be transmitted to the medical information management server 5, displaying of the medical information received from the medical information management server 5, a viewing request for the radiologic interpretation report to be transmitted to the radiologic interpretation report server 7, and displaying of the radiologic interpretation report received from the radiologic interpretation report server 7 are performed b executing software programs for the various processes.

The medical information management server 5 is realized by installing a software program that provides a function of a database management system (DBMS) on a general-purpose computer. The medical information management server 5 includes a large-capacity storage constituted by the medical information database 6. This storage may be a large-capacity hard disk device connected to the medical information management server 5 via a data bus, or may be a disk device connected to a network attached storage (NAS) and a storage area network (SAN) connected to the network 10. In a case where a registration request for medical information of the medical image from the modality 2 is received, the medical information management server 5 arranges the medical information in a database format, and registers the medical information in the medical information database 6.

In a case where the viewing request from the radiologic interpretation WS 3 and the hospital department WS 4 is received via the network 10, the medical information management server 5 searches for the medical information registered in the medical information database 6, and transmits the searched medical information to the radiologic interpretation WS 3 and the hospital department WS 4 which are requesting sources.

Image data of the medical image acquired in the modality 2 is registered, as one of the medical information, in the medical information database 6. Examination information is given, as accessory information, to the medical image. The accessory information includes, for example, an image identification (ID) for identifying an individual medical image, a patient ID for identifying a patient, an examination ID for identifying an examination, an examination date when the medical image is generated, an examination time, the kind of the modality used for the examination for acquiring the medical image, patient information such as a patient name, an age, and a gender, an examination part (imaged part), imaging information (imaging protocol, imaging sequence, imaging method, imaging condition, and using of a contrast agent), and information such as a series number or a collection number at the time of acquiring a plurality of medical images in one examination. At the time of acquiring the plurality of medical images in one examination, the plurality of medical images may be acquired by different modalities 2. For example, both a CT image and an MRI image may be acquired in one examination.

An analysis result for the medical image and clinical information of the patient are registered, as the medical information, in the medical information database 6. The analysis result for the medical image may be acquired in the priority judgement device included in the radiologic interpretation WS 3 to be described below, or may be acquired in an analysis device which is provided separately from the priority judgement device and is connected to the network 10. In a case where the medical image can be analyzed in the hospital department WS 4, the analysis result may be acquired in the hospital department WS 4.

Any information acquired for any period, such as information of symptoms such as pain and paralysis, a location of symptom, a time elapsing after symptoms occurs, and an age of the patient, which is acquired from a medical examination by interview, diagnosis, and an ambulance crew in a case where the patient is emergency transported can be used as the clinical information of the patient.

A differential image between a current medical image and a past medical image of the patient may be used at the time of diagnosis. In such a case, image data of the differential image is registered, as one of the medical information, in the medical information database 6.

The radiologic interpretation report server 7 is realized by installing a software program that provides a function of the database management system (DBMS) on the computer. In a case where a registration request for the radiologic interpretation report from the radiologic interpretation WS 3 is received, the radiologic interpretation report server 7 arranges the radiologic interpretation report in a database format, and registers the radiologic interpretation report in the radiologic interpretation report database 8.

For example, a radiologic interpretation report that records information such as an image ID for identifying the medical image of the radiologic interpretation target, a radiologist ID for identifying the radiologist who performs the radiologic interpretation, a lesion name, positional information of a lesion, a medical opinion, and a certainty factor of the medical opinion is registered in the radiologic interpretation report database 8.

As stated above, the priority judgement device according to the present embodiment is included in the radiologic interpretation WS 3. Thus, a priority judgement program according to the present embodiment is installed on the radiologic interpretation WS 3. The priority judgement program is distributed while being recorded in a recording medium such as DVD or CD-ROM, and is installed on a computer constituting the radiologic interpretation WS 3 from the recording medium. Alternatively, the application program is stored in a storage device of a server computer connected to a network or a network storage so as to be accessible from the outside, and is downloaded to and installed on the computer.

Figure 2:
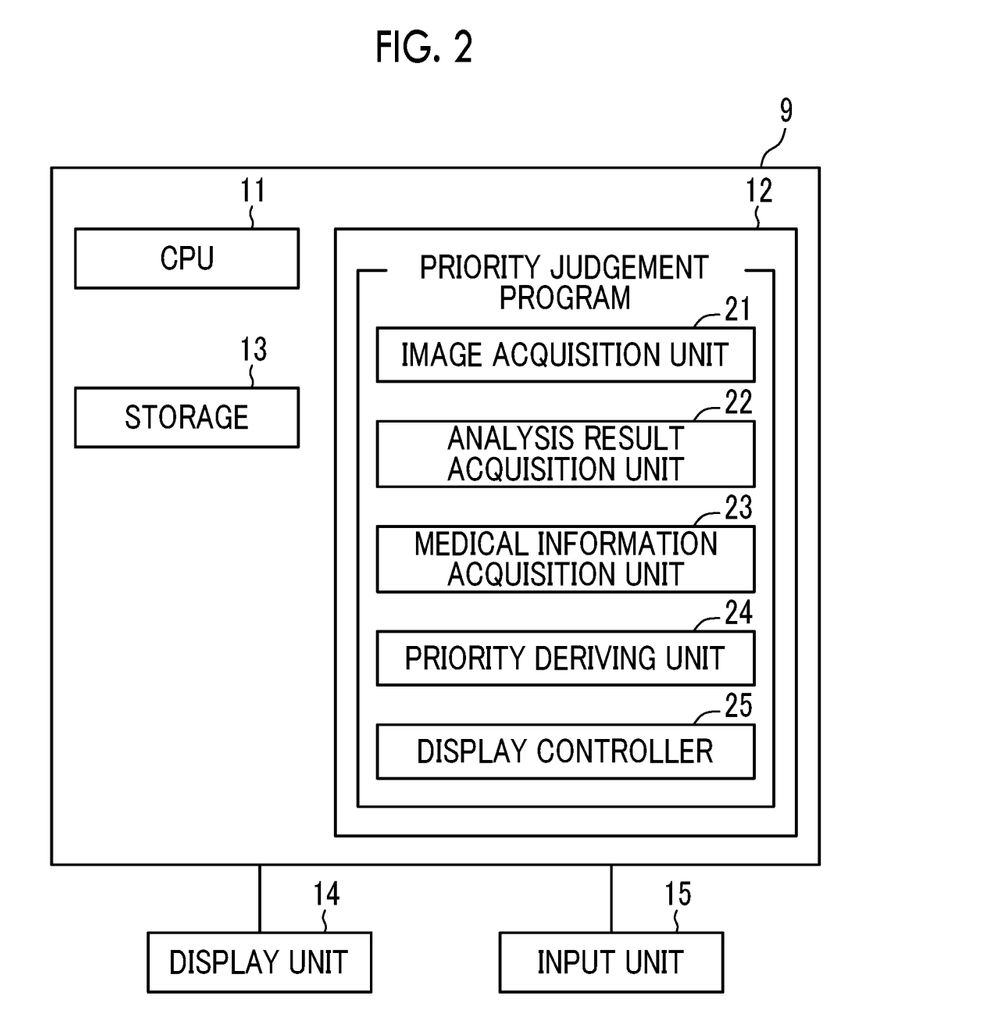
FIG. 2 is a diagram showing a schematic configuration of the priority judgement device according to the embodiment of the present disclosure.

FIG. 2 is a diagram showing a schematic configuration of the priority judgement device according to the present embodiment which is realized by installing the priority judgement program on the computer. As shown in FIG. 2, a priority judgement device 9 includes a central processing unit (CPU) 11, a memory 12, and a storage 13. A display unit 14 such as a liquid crystal display and an input unit 15 such as a keyboard and a mouse are connected to the priority judgement device 9.

The storage 13 is a storage device such as a hard disk or a solid state drive (SSD). Various information including the medical image, the medical information, and information required in the processing which are acquired from the medical information management server 5 via the network 10 are stored in the storage 13.

The priority judgement program is stored in the memory 12. The priority judgement program defines, as processes to be executed by the CPU 11, an image acquiring process of acquiring the medical image of the patient as a priority judgement target from the medical information management server 5, analysis result acquiring process of acquiring an analysis result by analyzing the medical image, a medical information acquisition process of acquiring medical information which is related to the medical image and is different from the medical image from the medical information management server 5, a priority deriving process of deriving a priority of the medical image based on the analysis result and the medical information, and a display control process of displaying information regarding the medical image and information of the priority in association with each other on the display unit 14.

The CPU 11 executes these processes according to the program, and thus, the computer functions as an image acquisition unit 21, an analysis result acquisition unit 22, a medical information acquisition unit 23, a priority deriving unit 24, and a display controller 25.

In a case where the radiologic interpretation WS 3 functions as a device that performs the processes other than the priority judgement device 9, the program for executing the function thereof is executed. For example, in a case where the radiologic interpretation of the medical image is performed, a radiologic interpretation program is executed.

The image acquisition unit 21 is a communication interface that communicates with the medical information management server 5 via the network 10, and acquires a medical image G0 of a patient as the priority judgement target from the medical information database 6 through the medical information management server 5 according to a command of the priority judgement program. In the present embodiment, the medical image is a CT image of the brain, but may be an MRI image.

The analysis result acquisition unit 22 acquires an analysis result R0 related to a disease included in the medical image by analyzing the medical image G0. In the present embodiment, the analysis result acquisition unit 22 acquires, as the analysis result R0, a certainty factor $P1i$ indicating that each pixel (voxel) of the medical image G0 is infarcted. It is preferably that the infarction is a hyperacute infarction within 24 hours from pathogenesis. Thus, the analysis result acquisition unit 22 includes a discriminator that performs machine learning so as to discriminate whether or not each pixel (voxel) of the CT image is infarcted. In the present embodiment, the discriminator is a neural network which performs deep learning so as to discriminate an infarcted region included in the medical image G0 which is the CT image. In a case where the medical image G0 which is the CT image is input, the discriminator learns so as to output, as the analysis result R0, a certainty factor $P1i$ indicating that each pixel (voxel) within the medical image G0 is infarcted. Here, the certainty factor $P1i$ is, for example, a value of 0 or more and 1 or less, and as the value becomes larger, there is a high possibility that the pixel is to be infarcted becomes higher.

The discriminator may be, for example, support vector machines (SVM), convolutional neural network (CNN), and recurrent neural network (RNN) in addition to the neural network that learns deep learning.

The image acquisition unit 23 is a communication interface that communicates with the medical information management server 5 via the network 10, and acquires medical information J0 which is related to a medical image G0 and is different from the medical image G0 as the priority judgement target from the medical information database 6 through the medical information management server 5 according to a command of the priority judgement program. In the present embodiment, it is assumed that an analysis result R1 of a diffusion-weighted image of the MRI acquired in the same examination as the medical image G0 as the priority judgement target is acquired as the medical information J0. The medical information J0 is a certainty factor $P2i$ indicating that each pixel of the diffusion-weighted image is infarcted. Similar to the certainty factor $P1i$, the certainty factor $P2i$ is also a value of 0 or more and 1 or less, and as the value becomes larger, there is a high possibility that the pixel is to be infarcted becomes higher. The diffusion-weighted image corresponds to another medical image of the present disclosure.

The analysis result acquisition unit 22 includes the discriminator that performs the machine learning so as to discriminate whether or not each pixel of the diffusion-weighted image of the MRI, and the medical information acquisition unit 23 may acquire the MRI image acquired in the same examination as the medical image G0 which is the CT image as the priority judgement target, and may generate the analysis result R1 of the acquired MRI image by using the analysis result acquisition unit 22. In this case, the medical information acquisition unit 23 acquires, as the medical information J0, the analysis result R1 generated by the analysis result acquisition unit 22.

The priority deriving unit 24 derives the priority of the medical image G0 based on the analysis result R0 and the medical information J0. In the present embodiment, since the priority is derived in the radiologic interpretation WS 3, the priority indicates that the radiologic interpretation is to be preferentially performed. Thus, the priority deriving unit 24 derives a total certainty factor $P1i \times P2i$ by multiplying the certainty factor $P1i$ and the certainty factor $P2i$ at positions corresponding to each other, and discriminates that this pixel is infarcted in a case where the total certainty factor $P1i \times P2i$ is equal to or greater than a predetermined threshold value Th1. The priority deriving unit 24 derives, as the priority, a total v1 of the pixels discriminated to be infarcted.

Here, on the diffusion-weighted image, a infarct region has a signal value higher (density lower) than that of another region, and a difference in signal value between the infarct region and another region is large. Meanwhile, on the CT image, the infarct region has a signal value lower (density higher) than that of another region, and a difference in signal value between the infarct region and another region is small. Thus, the infarct region on the diffusion-weighted image is easier to be seen than that on the CT image. Accordingly, the reliability of the certainty factor indicating that the pixel within the medical image G0 is infarcted becomes higher by multiplying the certainty factor $P1i$ of each pixel which is the analysis result R0 acquired from the medical image G0 which is the CT image by the certainty factor $P2i$ of each pixel which is the medical information J0 acquired from the diffusion-weighted image. Thus, there is a high possibility that the priority derived by the priority deriving unit 24 is to be infarcted.

Figure 3:
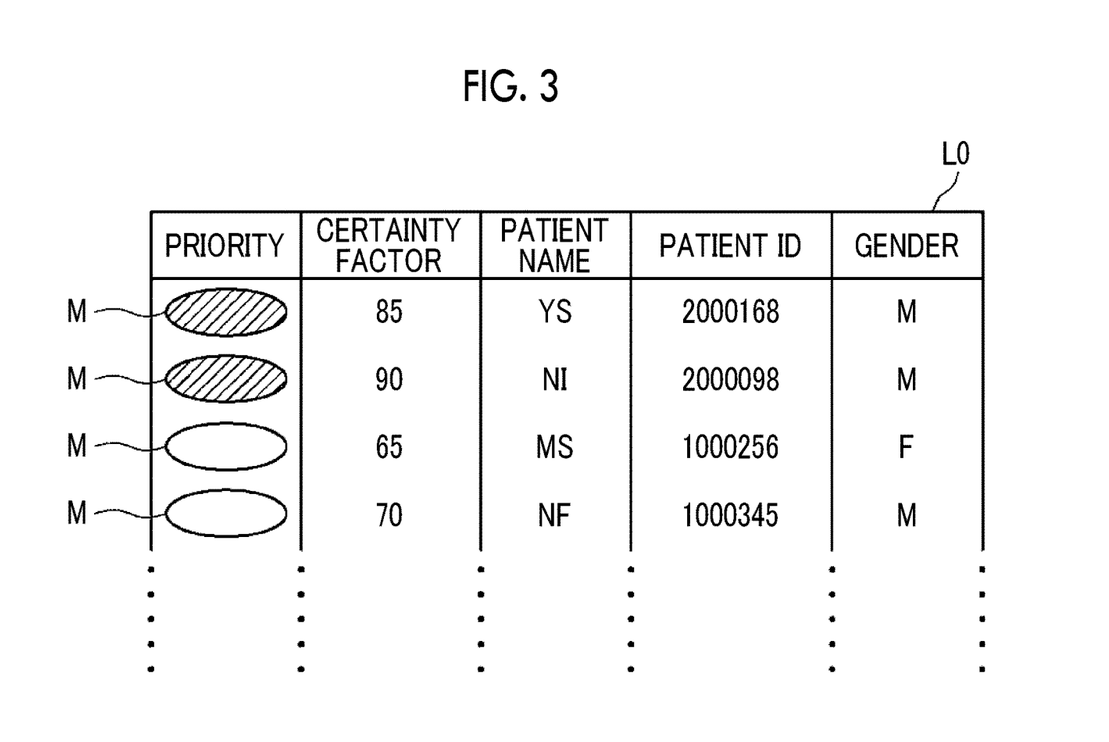
FIG. 3 is a diagram showing a list of information regarding a medical image and information of a priority.

The display controller 25 generates a list in which the information regarding the medical image G0 and the information of the priority are associated with each other for the plurality of medical images, and displays the generated list on the display unit 14. FIG. 3 is a diagram showing the list in which the information regarding the medical image and the information of the priority are associated with each other. A priority, a certainty factor, a patient name, a patient ID, and a gender are included in a list L0 as shown in FIG. 3. A priority column in the list L0 indicates the priority derived by the priority deriving unit 24, and a certainty factor column in the list L0 indicates the certainty factor Pi1 generated by the analysis result acquisition unit 22. At least one of the patient name, the patient ID, and the gender is information regarding the medical image. The information included in the list is not limited thereto, and may include information such as an examination date, an examination technician, and a doctor.

A mark M having a horizontally long oval shape is represented in the priority column of the list L0 shown in FIG. 3. The display controller 25 gives a color to the mark M for the medical image of which the priority is equal to or greater than a predetermined threshold value Th1. In FIG. 3, a state in which the color is given is depicted by a diagonal line. For example, any color such as red and yellow may be used as the color. The patient name of which the priority is equal to or greater than the threshold value Th1 may be turned on and off by changing the color. Any color is not given to the mark M of the medical image of which the priority is less than the threshold value Th1. Accordingly, the radiologist can recognize which medical image of the plurality of medical images included in the list L0 is to be preferentially interpreted by seeing the list L0 displayed on the display unit 14.

The network 10 is a wired or wireless local area network that connects various devices within a hospital. In a case where the radiologic interpretation WS 3 and the hospital department WS 4 are installed in another hospital or a clinic, the network 10 may connect local area networks of hospitals via the Internet or a dedicated line.

Figure 4:
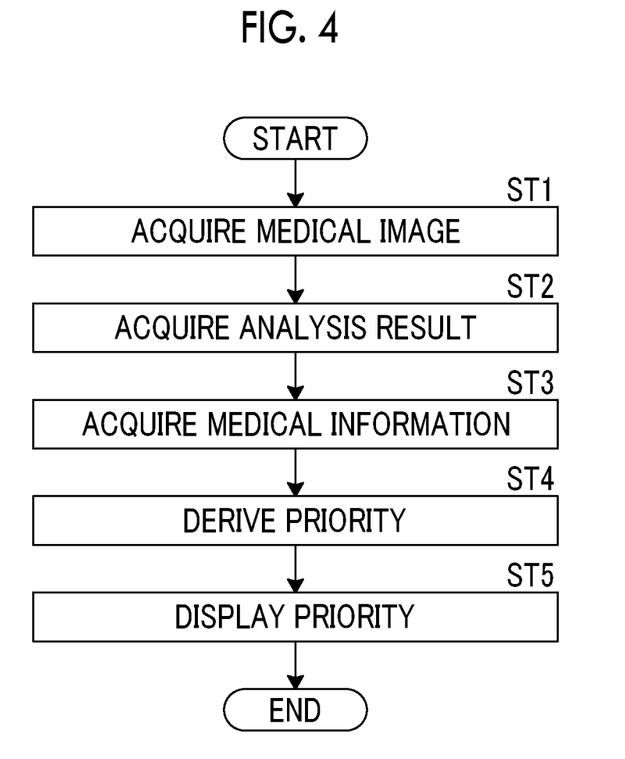
FIG. 4 is a flowchart showing processes performed in the present embodiment.

Next, processes performed in the present embodiment will be described. FIG. 4 is a flowchart showing processes performed by the priority judgement device 9 included in the radiologic interpretation WS 3 in the present embodiment. Initially, the image acquisition unit 21 acquires the medical image G0 of the patient as the priority judgement target (step ST1). Subsequently, the analysis result acquisition unit 22 acquires the analysis result R0 by analyzing the medical image G0 (step ST2). The medical information acquisition unit 23 acquires the medical information J0 different from the medical image G0 from the medical information management server 5 (step ST3). The priority deriving unit 24 derives the priority of the medical image G0 based on the analysis result R0 and the medical information J0 (step ST4). The display controller 25 displays the information regarding the medical image and the information of the priority in association with each other for the plurality of medical images on the display unit 14 (priority display; step ST5), and ends the process.

As stated above, in the present embodiment, the analysis result R0 for the medical image G0 as the priority judgement target is acquired, the medical information J0 which is related to the medical image G0 and is different from the medical image G0 is acquired, and the priority of the medical image G0 is derived based on the analysis result R0 and the medical information J0. Thus, it is possible to appropriately judge the priority at the time of radiologic interpretation of the medical image G0 and examining and treating the patient while referring to the derived priority.

In particular, since the list in which the information regarding the medical image and the information of the priority are associated with each other for the plurality of medical images is generated and the generated list is displayed on the display unit 14, the radiologist can easily recognize which medical image of the plurality of medical images is to be preferentially interpreted.

In the aforementioned embodiment, the priority derived by the priority deriving unit 24 may be transmitted to the medical information management server 5, and may be registered in association with the medical image in the medical information database 6. Accordingly, the terminal such as the hospital department WS 4 other than the radiologic interpretation WS 3 connected to the network 10 can generate the list L0 shown in FIG. 3 similar to the radiologic interpretation WS 3, and display the generated list by acquiring the priority together with the medical image. In the aforementioned embodiment, the list L0 generated by the display controller 25 may be registered in the medical information database 6. Accordingly, the terminal such as the hospital department WS 4 other than the radiologic interpretation WS 3 connected to the network 10 can display the list L0 shown in FIG. 3 by acquiring the list L0. Accordingly, a medical examiner can easily recognize which patient for the medical image is acquired is to be preferentially diagnosed and treated.

Although it has been described in the aforementioned embodiment that the analysis result acquisition unit 22 of the priority judgement device 9 acquires the analysis result by analyzing the medical image G0, the present disclosure is not limited thereto. The medical image may be analyzed by an analysis device provided separately from the priority judgement device 9, and the analysis result acquired by the analysis device may be acquired by the analysis result acquisition unit 22. The hospital department WS 4 may analyze the medical image. In such a case, the analysis result acquired by the hospital department WS 4 may be acquired by the analysis result acquisition unit 22 of the priority judgement device 9. In a case where the analysis result is registered in the medical information database 6, the analysis result acquisition unit 22 may acquire the analysis result from the medical information database 6.

In the aforementioned embodiment, the priority judgement program according to the present embodiment may be installed on the hospital department WS 4. In this case, the priority is derived in the hospital department WS 4, and the information of the priority and the information of the medical image are displayed in association with each other.

In the aforementioned embodiment, a dedicated terminal that executes the priority judgement program according to the present embodiment may be separately installed as the priority judgement device. In this case, the priority derived in the priority judgement device separately installed is registered in the medical information database 6, and is used for generating and displaying the list L0 shown in FIG. 3 in the radiologic interpretation WS 3 and the hospital department WS 4. In the priority judgement device separately installed, the list L0 may be generated, and may be registered in the medical information database 6.

Although it has been described in the aforementioned embodiment that the CT image is used as the medical image G0 and the analysis result R1 of the diffusion-weighted image of the MRI is used as the medical information J0, the present disclosure is not limited thereto. The CT image may be used as the medical image G0, and the clinical information of the patient may be used as the medical information J0. Specifically, information indicating which side of left and right sides of the body is paralyzed may be used as the clinical information of the patient. Here, in a case where the right side of the body is paralyzed, there is a high possibility that the left brain is to be infarcted. Thus, for example, in a case where the clinical information of "right side is paralyzed" is acquired, the priority deriving unit 24 sets a weighting factor that allows a certainty factor P3$i$ of the infarction in a left brain region of the medical image G0 to be greater than another region, and weights the certainty factor P1$i$ of the position corresponding to each other by using the weighting factor. In a case where the weighted certainty factor P1$i$ is equal to or greater than a predetermined threshold value Th2, it is discriminated that this pixel is infarcted, and a total V2 of the pixels discriminated to be infarcted is derived as the priority. In this case, the infarction may also be a hyperacute infarction.

In this case, it is possible to appropriately judge the priority at the time of radiologic interpretation of the medical image and examining and treating the patient while referring to the priority.

In the aforementioned embodiment, a certainty factor P4$i$ of subarachnoid hemorrhage in the CT image may be acquired, as the analysis result R0, by the analysis result acquisition unit 22. In this case, the clinical information for specifying whether the subarachnoid hemorrhage is caused due to a traumatic injury or an aneurysm rupture may be used as the medical information J0. In this case, it is assumed that the priority deriving unit 24 derives the priority so as to be proportional to the total of pixels for which the certainty factor P4$i$ is equal to or greater than a predetermined threshold value Th3. In a case where the clinical information is aneurysm rupture, the threshold value Th3 is set to be small, and the priority is set to be large.

In this case, it is possible to appropriately judge the priority at the time of radiologic interpretation of the medical image and examining and treating the patient while referring to the priority.

In the aforementioned embodiment, in a case where the medical image as the priority judgement target is a differential image between medical images for which imaging dates are different for the same patient, the urgency of the radiologic interpretation is not so high. Thus, in a case where the medical image is the differential image, the priority deriving unit 24 may multiply the derived priority by the weighting factor for decreasing the priority.

In the aforementioned embodiment, for example, various processors to be described below can be used as hardware structures of the processing units that perform various processes such as the image acquisition unit 21, the analysis result acquisition unit 22, the medical information acquisition unit 23, the priority deriving unit 24, and the display controller 25. As stated above, examples of various processors include a programmable logic device (PLD) such as a field programmable gate array (FPGA) which is a processor of which a circuit configuration can be changed after being manufactured, a dedicated electric circuit such as an application specific integrated circuit (ASIC) which is a processor having a circuit configuration designed as a dedicated circuit in order to perform a specific process in addition to the CPU which is a general-purpose processor functioning as various processing units by executing software (program).

One processing unit may be constituted by one of these various processors, or may be constituted by a combination (for example, a combination of a plurality of FPGAs or a combination of the CPU and the FPGA) of the same kind or different kinds of two or more processors. Alternatively, the plurality of processing units may be constituted by one processor.

Firstly, as the example in which the plurality of processing units is constituted by one processor, there is a form in which one processor is constituted by a combination of one or more CPUs and software and this processor functions as the plurality of processing units as represented by computers such as a client and a server. Secondly, there is a form in which a processor that implements the entire system function including the plurality of processing units by one integrated circuit (IC) chip as represented by a system on chip (SoC) is used. As stated above, various processing units are constituted as hardware structure by using one or more of various processors.

More specifically, an electric circuitry acquired by combining circuit elements such as semiconductor elements can be used as the hardware structure of these various processors.

What is claimed is:

1. A priority judgement device adapted to judge a priority of performing radiologic interpretation of a medical image, the priority judgement device comprising:
    a processor, configured to:
        acquire an analysis result for the medical image, wherein the medical image is a subject of priority judgement;
        acquire medical information which is related to the medical image, wherein the medical information is different from the medical image; and
        derive a priority of performing the radiologic interpretation of the medical image based on the analysis result and the medical information,
    wherein the medical image is a CT image,
    the processor acquires, as the analysis result, a first certainty factor for each pixel of the CT image indicating a certainty that each pixel of the CT image is infarcted,
    the processor acquires, as the medical information, a second certainty factor for each pixel of an MRI image of a patient indicating a certainty that each pixel of the MRI image of the patient for which the medical image is acquired is infarcted, and
    the processor derives a higher priority as the number of pixels of which a total certainty factor based on the first certainty factor and the second certainty factor is equal to or greater than a predetermined first threshold value becomes larger on the CT image.

2. The priority judgement device according to claim 1, further comprising:
    a display controller that displays information regarding the medical image and information of the priority in association with each other for a plurality of the medical images on a display.

3. The priority judgement device according to claim 1, wherein the infarction is a hyperacute infarction.

4. A priority judgement device adapted to judge a priority of performing radiologic interpretation of a medical image, the priority judgement device comprising:
    a processor, configured to:
        acquire an analysis result for the medical image, wherein the medical image is a subject of priority judgement;

acquire medical information which is related to the medical image, wherein the medical information is different from the medical image; and derive a priority of performing the radiologic interpretation of the medical image based on the analysis result and the medical information, wherein the medical image is a CT image, the processor acquires, as the analysis result, a first certainty factor for each pixel of the CT image indicating a certainty that each pixel of the CT image is infarcted, the processor acquires, as the medical information, part information indicating a paralyzed part of a patient for which the medical image is acquired, and the processor weights the first certainty factor according to the part information, and derives a higher priority as the number of pixels of which the weighted first certainty factor is equal to or greater than a predetermined second threshold value becomes larger on the CT image.

5. The priority judgement device according to claim 4, further comprising:

a display controller that displays information regarding the medical image and information of the priority in association with each other for a plurality of the medical images on a display.

6. A priority judgement device adapted to judge a priority of performing radiologic interpretation of a medical image, the priority judgement device comprising:

a processor, configured to:

acquire an analysis result for the medical image, wherein the medical image is a subject of priority judgement;

acquire medical information which is related to the medical image, wherein the medical information is different from the medical image; and derive a priority of performing the radiologic interpretation of the medical image based on the analysis result and the medical information, wherein the medical image is a CT image, the processor acquires, as the analysis result, a bleeding certainty factor for each pixel of the CT image indicating a certainty that each pixel of the CT image is a subarachnoid hemorrhage region, the processor acquires, as the medical information, clinical information indicating whether subarachnoid hemorrhage is caused by traumatic bleeding or an aneurysm rupture for a patient for which the medical image is acquired, and the processor sets a predetermined third threshold value to be low, in a case where the clinical information is the aneurysm rupture at the time of deriving a higher priority as the number of pixels of which the bleeding certainty factor is equal to or greater than the third threshold value becomes larger on the CT image.

7. The priority judgement device according to claim 6, further comprising:

a display controller that displays information regarding the medical image and information of the priority in association with each other for a plurality of the medical mages on a display.

* * * * *